United States Patent
Arora

(10) Patent No.: US 10,588,823 B1
(45) Date of Patent: Mar. 17, 2020

(54) SYSTEM FOR THE TRACKING, DISPENSING, AND ADMINISTERING OF A MEDICAMENT IN A PROGRAMMABLE ENCAPSULATION

(71) Applicant: Rakesh Arora, Somerset, NJ (US)

(72) Inventor: Rakesh Arora, Somerset, NJ (US)

(*) Notice: Subject to any disclaimer, the term of this patent is extended or adjusted under 35 U.S.C. 154(b) by 11 days.

(21) Appl. No.: 16/018,792

(22) Filed: Jun. 26, 2018

Related U.S. Application Data

(60) Provisional application No. 62/531,559, filed on Jul. 12, 2017.

(51) Int. Cl.
| | | |
|---|---|---|
| *A61J 3/07* | (2006.01) | |
| *A61J 7/04* | (2006.01) | |
| *A61J 3/06* | (2006.01) | |
| *G07F 17/00* | (2006.01) | |
| *A61J 7/02* | (2006.01) | |
| *A61J 3/00* | (2006.01) | |

(52) U.S. Cl.
CPC .... *A61J 3/07* (2013.01); *A61J 3/06* (2013.01); *A61J 7/0454* (2015.05); *A61J 7/0481* (2013.01); *A61J 3/007* (2013.01); *A61J 7/02* (2013.01); *A61J 7/0427* (2015.05); *G07F 17/0092* (2013.01)

(58) Field of Classification Search
CPC .. A61J 2200/30; A61J 7/0076; A61J 2205/60; A61J 3/07; A61J 7/0454; A61J 3/06; A61J 7/0481; G06F 19/3462; A61M 31/002
USPC ........................................................ 340/10.51
See application file for complete search history.

(56) References Cited

U.S. PATENT DOCUMENTS

| | | | |
|---|---|---|---|
| 7,080,755 B2 | 7/2006 | Handfield et al. | |
| 7,253,716 B2 | 8/2007 | Lovoi et al. | |
| 7,504,954 B2 | 3/2009 | Spaeder | |
| 7,796,043 B2 | 9/2010 | Euliano et al. | |
| 8,115,618 B2 | 2/2012 | Robertson et al. | |
| 8,540,632 B2 | 9/2013 | Robertson et al. | |
| 8,912,908 B2 * | 12/2014 | Berkman ............. | A61B 5/0538 340/573.1 |

(Continued)

OTHER PUBLICATIONS

Medminder, Pill Dispenser, Website, May 16, 2018, 7 pages, https://www.medminder.com/.

(Continued)

*Primary Examiner* — Eric Blount
(74) *Attorney, Agent, or Firm* — Goldstein Law Offices, P.C.

(57) ABSTRACT

A system comprising one or more of a programmable encapsulation for containing and regulating the release of a medicament, an encapsulating device used by a manufacturer which encloses the medicament within a programmable encapsulation, a programming device used by a pharmacy or dispensary which programs the encapsulation with an intended patient's health data and prescription data, a consumer encapsulation storage device configured to store one or more programmable encapsulations for one or more of a patient, authenticate the identity of a patient, and dispense medicaments to the patient in accordance with the patient's prescription, and a portable reader configured to scan a programmable encapsulation and display the details of the medicament and instructions for its consumption.

1 Claim, 10 Drawing Sheets

(56) References Cited

U.S. PATENT DOCUMENTS

| | | | |
|---|---|---|---|
| 8,945,005 B2* | 2/2015 | Hafezi | A61B 5/073 |
| | | | 600/300 |
| 9,183,724 B2 | 11/2015 | Covannon et al. | |
| 9,270,025 B2* | 2/2016 | Robertson | A61B 5/0031 |
| 9,327,076 B2 | 5/2016 | Trovato et al. | |
| 9,662,392 B2* | 5/2017 | Altschul | H05K 999/99 |
| 9,883,819 B2* | 2/2018 | Jensen | A61B 5/0002 |
| 10,010,703 B2* | 7/2018 | Altschul | A61K 31/58 |
| 10,292,642 B2* | 5/2019 | Euliano | G08B 23/00 |
| 2006/0071011 A1 | 4/2006 | Varvarelis et al. | |
| 2006/0289640 A1* | 12/2006 | Mercure | A01K 11/007 |
| | | | 235/435 |
| 2008/0114490 A1* | 5/2008 | Jean-Pierre | G06F 19/3462 |
| | | | 700/241 |
| 2014/0028454 A1 | 1/2014 | Covannon et al. | |
| 2015/0343144 A1* | 12/2015 | Altschul | H05K 999/99 |
| | | | 604/503 |

OTHER PUBLICATIONS

Pilldrill, Smart Medication Tracking That Simply Works, Website, May 16, 2018, 3 pages, https://www.pilldrill.com/.

* cited by examiner

| 901 | Ingestion State | Release State |
|---|---|---|
| 908  E | 06:02, True | Deactivated |
| 907  D | 06:01, True | Deactivated |
| 906  C | 05:01, True | 09:15, False |
| 905  B | 05:00, True | 05:15, True |
| 904  A | 01:00, True | 01:15, True |

Current Time: 06:10    10mg/4hrs

Dose Timeline

SYSTEM FOR THE TRACKING, DISPENSING, AND ADMINISTERING OF A MEDICAMENT IN A PROGRAMMABLE ENCAPSULATION

CROSS-REFERENCE TO RELATED APPLICATIONS

This application is a nonprovisional utility application of provisional patent application, Ser. No. 62/531,559 filed in the United States Patent Office on Jul. 12, 2017, claims priority therefrom, and is expressly incorporated herein by reference in its entirety.

TECHNICAL FIELD

The present disclosure relates generally to a system for tracking, dispensing, and administering a medicament in a programmable encapsulation. More particularly, the present disclosure relates to a system for managing one or more of a medicament contained within a programmable encapsulation at all stages of its life cycle from manufacture to consumption, and methods for its use.

BACKGROUND

The consumption of prescription medicaments is a routine activity in everyday life, but is also an activity in which a small mistake can have devastating consequences. A patient in need of a prescription medicament must trust that the doctor has prescribed a medicament that is safe for the patient and that the pharmacy has dispensed the correct medicaments at the proper dosage. The patient must further carefully consume the correct medicaments at the scheduled times in accordance with the prescription. When a patient has been prescribed more than one medicament at a time, the opportunity for human error to occur at some point in the process is greatly increased. The prescribing doctor may be unaware of a medicament that was prescribed for the patient by another doctor and may unwittingly prescribe a medicament that would trigger a dangerous drug interaction. An error at the pharmacy can result in the patient being dispensed the wrong medicaments. The patient, faced with having to consume multiple medicaments in confusingly similar encapsulations, may accidentally take too many of one medicament and experience an overdose, or may miss a vital dose altogether. Furthermore, there are the dangers caused by counterfeit medicaments making their way into the pharmaceutical supply chain, as well as the opportunity for improper or illegal usage of prescription medicaments by someone who is not the patient for whom the medicament was prescribed. There is a pressing need for a system that allows prescription medicaments to be safely prescribed, dispensed, and administered while also curtailing the dangers caused by counterfeit medicaments and illegal and improper consumption.

There are various devices in the prior art which attempt to address some of these problems. There are examples of smart pills within the prior art which are designed to prevent an overdose of a medicament. There are also devices for organizing medicaments and dispensing them to patients at predetermined times. Furthermore, there are existing systems which allow patient health information to be aggregated to assist in creating a coordinated medical treatment plan for a patient.

While these units may be suitable for the particular purpose employed, or for general use, they would not be as suitable for the purposes of the present disclosure as disclosed hereafter. The examples found in the prior art do not provide a unified system that can track medicaments and ensure that they are safely prescribed, dispensed, and consumed, while providing redundant safety checks at the dispensing and consumption levels.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a system which allows for a medicament contained within a programmable encapsulation to be tracked, properly dispensed, and safely consumed. Accordingly, the present disclosure provides a system comprising one or more of a programmable encapsulation containing a medicament, as well as a plurality of devices deployed at the manufacturer, dispensary, and consumer levels which are configured to track, program, and dispense the programmable encapsulation across each stage of the medicament's life cycle from manufacture to consumption, allowing the correct medicament to be dispensed to its intended patient. Each programmable encapsulation is configured to release its medicament only in accordance with the patient's prescription in order to prevent improper doses or overdoses, and can further be configured to verify that the person ingesting the encapsulation is the intended patient before releasing any medicaments. In addition, the system is designed to deter the use of counterfeits, and prevent programmable encapsulations from being diverted and used illegally.

It is another aspect of an example embodiment in the present disclosure to provide a system comprising one or more of a programmable encapsulation for containing and regulating the release of a medicament, an encapsulating device used by a manufacturer which encloses the medicament within a programmable encapsulation, a programming device used by a pharmacy or dispensary which programs the encapsulation with an intended patient's health data and prescription data, a consumer encapsulation storage device configured to store one or more medicaments for one or more of a patient, authenticate the identity of a patient, and dispense medicaments to the patient in accordance with the patient's prescription, and a portable reader configured to scan a programmable encapsulation and display the details of the medicament and instructions for its consumption.

It is yet another aspect of an example embodiment in the present disclosure to provide an encapsulating device which encapsulates a medicament within a programmable encapsulation and permanently encodes the encapsulation with a unique identifier which conveys the manufacturing process information and the formulation of the encapsulated medicament. The unique identifier not only helps prevent the misidentification of the medicament, but also helps deter counterfeiting by showing that the encapsulation is authentic.

It is a further aspect of an example embodiment in the present disclosure to provide a programmable encapsulation comprising a medicament component for storing and releasing a medicament, and an encapsulation control module having an RF module, sensors, processing unit, and power source. The encapsulation control module is configured to communicate with other programmable encapsulations and system devices, monitor the condition of the encapsulation, and regulate the release of the medicament. Each encapsulation can transmit as well as receive an RF signal conveying the formulation of the enclosed medicament along with other details regarding the status of the encapsulation, such as the time it was ingested by the patient, and whether the enclosed medicament has been released. This allows the encapsulation to communicate with other system devices, detect other encapsulations within a patient's body, and release the medicament at the proper time according to the prescription data, as well as prevent the release of the encapsulated medicament in order to avoid an overdose, improper dose, or a dangerous reaction with another medicament. The encapsulation can also be configured to prevent improper or illegal use by becoming operational only when it is programmed with a patient's health data and prescription data via a programming device at an authorized dispensary or pharmacy. The encapsulation can also be configured to release the medicament only when ingested by the patient for whom the medicament was prescribed.

It is yet an additional aspect of an example embodiment in the present disclosure to provide a programming device deployed at a dispensary which is configured to receive a patient's health data and prescription data, verify that a medicament selected to fill the patient's prescription is of the correct formulation by electronically reading the unique identifier encoded within programmable encapsulation containing the medicament, and program each programmable encapsulation containing the medicament with the patient's health data and prescription data. The programming device can be further configured to reference the patient's health data to provide a warning if the patient is allergic to the prescribed medicament, or if consuming the prescribed medicament may trigger a dangerous interaction with another medicament used by the patient.

It is yet a further aspect of an embodiment of the present disclosure to provide a consumer encapsulation storage device for storing and dispensing one or more of a programmable encapsulation. After a patient receives programmable encapsulations containing prescribed medicaments from a pharmacy or dispensary, the patient can store the encapsulations in a consumer encapsulation storage device for later dispensing. The consumer encapsulation storage device can securely store each encapsulation and dispense an encapsulation only to the intended patient, in accordance with the prescription's dosage schedule. The consumer encapsulation storage device can be configured with a variety of biometric sensors for verifying the patient's identity. The consumer encapsulation storage device can further be configured to store and dispense medicaments for more than one patient. The system can further incorporate a portable reader which allows a patient to scan a programmable encapsulation in order to identify the enclosed medicament and obtain prescription information and instructions for its consumption.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

FIG. 9 is a chart depicting an example of a dose timeline governing the operation of a plurality of ingested encapsulations, in accordance with an embodiment of the present disclosure.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
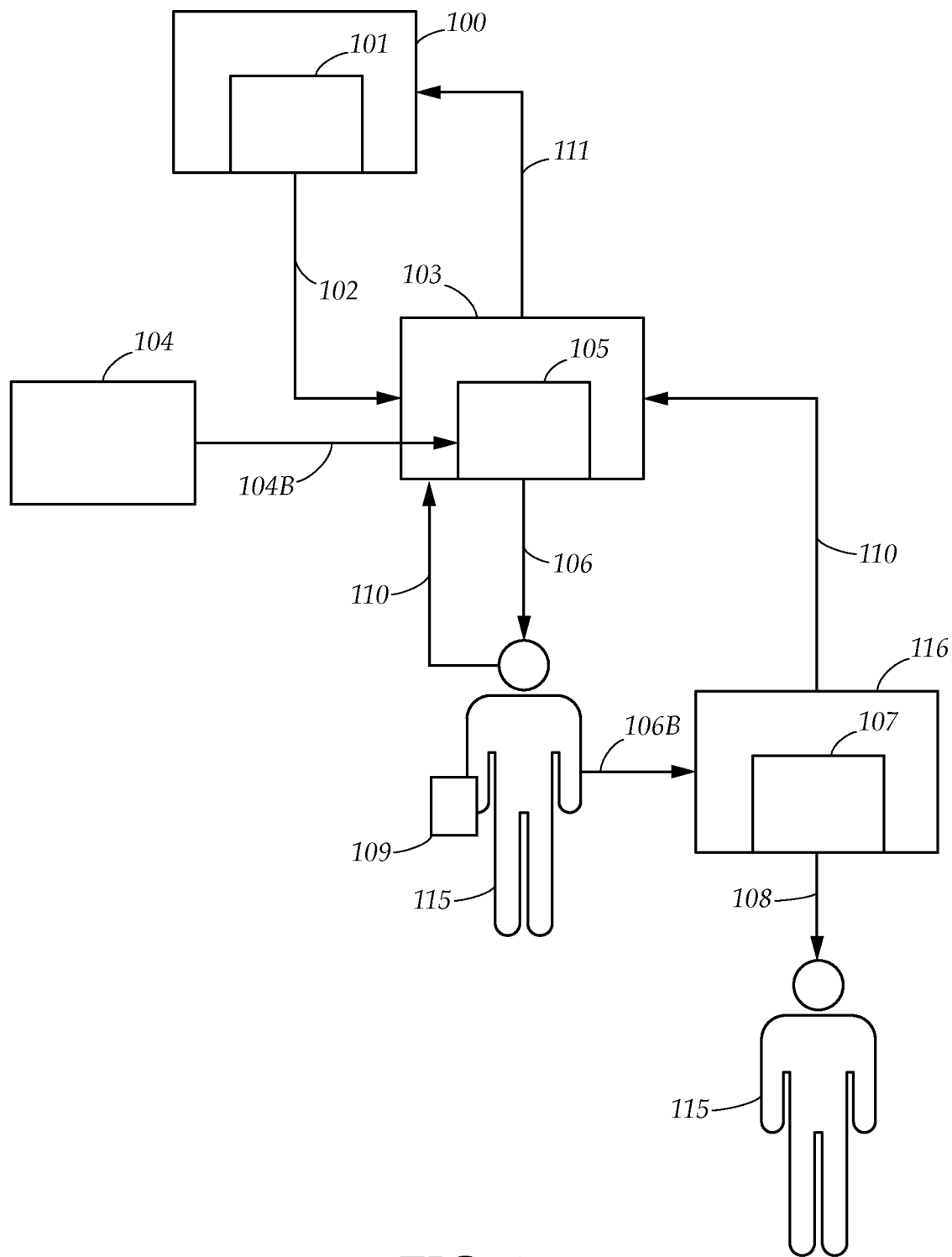
FIG. 1 is a block diagram depicting the operation of a plurality of devices which comprise the system, in accordance with an embodiment of the present disclosure.

FIG. 1 illustrates the general operation of a system in accordance with an aspect of an embodiment of the present disclosure. An encapsulating device 101 deployed at a manufacturing facility 100 encapsulates one or more of a medicament within a programmable encapsulation and encodes within each encapsulation a unique identifier indicating the formulation of the medicament enclosed within along with manufacturing process information such as the identity of the manufacturer, time of manufacture, batch number, expiration date, as well as other relevant information. Each encapsulation can be uniquely identified by its unique identifier. Each encapsulation is then packaged and distributed 102 to a dispensary 103, which can be a hospital, pharmacy, clinic, or other suitable facility. Before a dispensary distributes any medicaments to a patient 115, it first receives from a prescriber 104 a patient data profile 104B containing the patient's health data, and prescription data detailing a prescribed medicament. The patient data profile can be received electronically from the prescriber or it can be created manually at the dispensary by having the patient provide a traditional written prescription along with the relevant details about the patient's health. The dispensary selects one or more of a programmable encapsulation containing the prescribed medicament, and then employs a programming device 105 deployed at the dispensary to verify each encapsulation. The programming device scans each encapsulation to ensure that the formulation of the enclosed medicament matches the patient's prescription data, programs each encapsulation with the patient profile data, and activates each encapsulation for use. Each activated programmable encapsulation is then distributed 106 to the patient. Upon receiving one or more of a programmable encapsulation, the patient can store 106B each programmable encapsulation within a consumer encapsulation storage device 107 which can be deployed at a location 116 of the patient's choosing, such as the patient's home. A consumer encapsulation storage device can be configured to store, organize, and dispense 108 medicaments for one or more patients in accordance with each patient's prescription data. The consumer encapsulation storage device can be configured to verify the identity of the patient before dispensing any medicaments, by employing biometric tests such as fingerprint, iris, or retina scans, facial recognition, or other suitable tests, in order to ensure that medicaments are only dispensed to the patient for whom it was prescribed. A portable reader 109 is configured to scan and read the data on a programmable encapsulation and display the details of the formulation of the enclosed medicament and instructions for its consumption in accordance with the prescription data programmed within. The portable reader therefore allows the patient to identify and pick programmable encapsulations without relying on a consumer encapsulation storage device. The system further allows for unused encapsulations to be returned 110 to the dispensary 103, where they can be sterilized and reprogrammed, or otherwise returned to the manufacturer 111.

Figure 2:
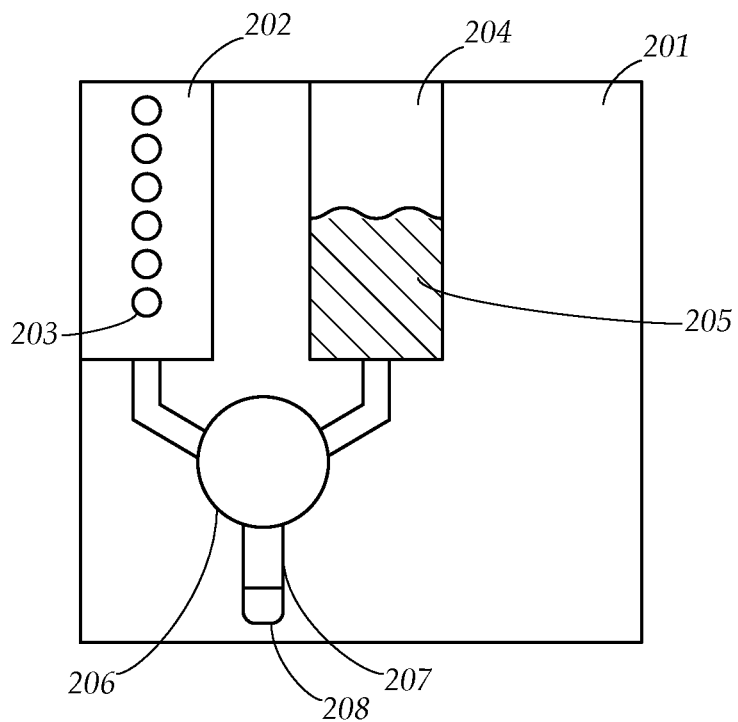
FIG. 2 is a diagrammatical cross section depicting an encapsulating device, in accordance with an embodiment of the present disclosure.

FIG. 2 depicts an embodiment of an encapsulating device 201 in accordance with an aspect of the present disclosure. The encapsulating device 201 is configured with one or more of an encapsulation chamber 202 containing a plurality of programmable encapsulations 203 which have yet to receive a medicament, and one or more of a medicament holding area 204 containing a plurality of a medicament 205. The encapsulating device is further configured with an encapsulation mechanism 206 which receives a programmable encapsulation from an encapsulation chamber 202, a medicament from a medicament holding area 205, and encapsulates the medicament within the programmable encapsulation. Next, the newly filled programmable encapsulation is encoded with a unique identifier using an encoding mechanism 207. The encoding mechanism 207 can be configured with an RFID writer 208 for writing data to the memory of the programmable encapsulation. In other embodiments of the present disclosure, the encoding mechanism can be configured to insert a pre-encoded read-only memory module containing the unique identifier into the encapsulation. The encapsulating device can further be configured with an engraving mechanism for engraving or printing the unique identifier onto the surface of a programmable encapsulation either in an alphanumeric form or as a coded representation such as a barcode or matrix code.

Figure 3:
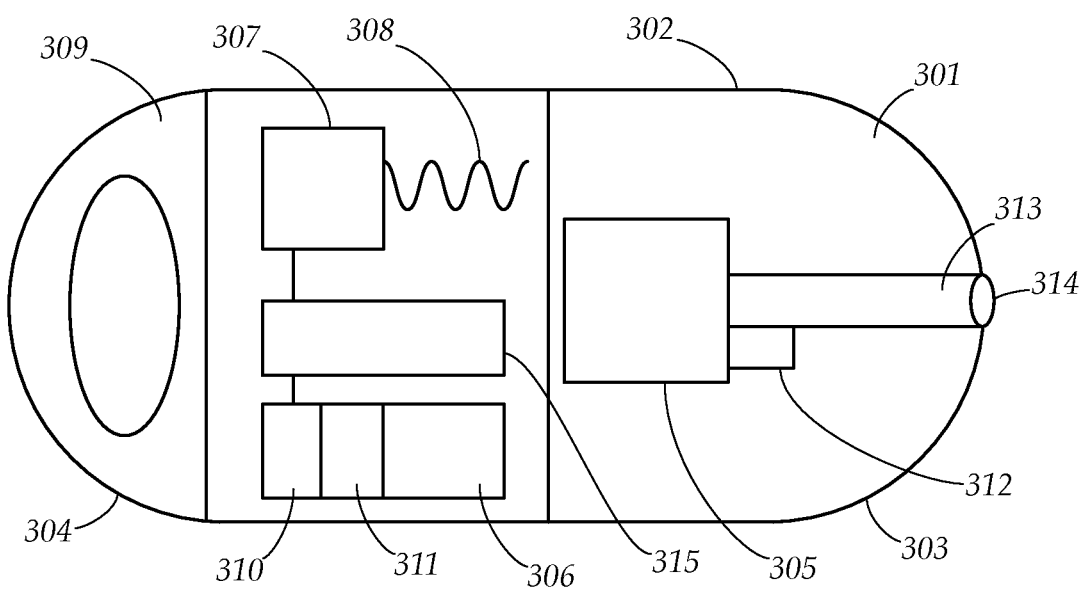
FIG. 3 is a diagrammatical cross section depicting a programmable encapsulation, in accordance with an embodiment of the present disclosure.

FIG. 3 illustrates an example embodiment of a programmable encapsulation 301 in accordance with the present disclosure. The programmable encapsulation comprises a shell 302 having a medicament component 303 and an encapsulation control module 304. The shell 302 can be made of an inert or indigestible material which is safe for ingestion. The medicament component 303 is configured with a medicament chamber 305 which can store at least one of a medicament. The encapsulation control module 304 is configured with a processing unit 306 which controls the functions of the encapsulation, comprising a clock, processor, and one or more of a memory. The encapsulation is further configured with an RF Transceiver 307 and antenna 308, allowing the encapsulation to transmit and receive RF signals to communicate with system devices and other programmable encapsulations. The RF Transceiver can employ a transmission technology such as passive or active RFID, or other technology suitable for use in a small scale device with low power requirements for transmitting signals over short distances. The encapsulation is further configured with a sensor module 309 which allows the encapsulation to determine whether it has been ingested by the patient, such as by detecting the presence of gastrointestinal fluids, and track the course of its progress through the patient's gastrointestinal tract. The sensor module 309 can further allow the encapsulation to detect whether it has exited the patient's body. The encapsulation also has a permanent storage 310 for storing a unique identifier, as well as a programmable storage 311 for storing the patient's health data and prescription data. Data within the permanent storage 310 cannot be altered except by the manufacturer's encapsulating device, to preserve the integrity of the unique identifier by preventing tampering. The programmable storage 311 is likewise protected through the use of encryption, password authentication, or a combination thereof. Protecting the data within the programmable storage secures the patient's health data and prescription data which is sensitive and private, and prevents an unauthorized party from reading the data without the decryption key. Similarly, restricting write access to the programmable storage is necessary to prevent unauthorized parties, including the patient, from tampering with the patient health data in order to reprogram the encapsulation for use by a different user or alter the prescription data. The encapsulation control module is further configured with a power source 315, which can be a miniaturized battery. The battery can be a rechargeable battery further configured to draw power from an external source using wireless power transfer. The processing unit 306 is configured to send a signal causing the medicament component 303 to release the medicament contained within the medicament chamber 305. The medicament can be released through a variety of means. In one embodiment of the present disclosure, the medicament is stored within the medicament chamber 305 in a liquid form, and is drawn from the medicament chamber by means of a miniaturized pump mechanism 312, and pumped into a release channel 313. The release channel leads to a gate 314 leading outside of the shell 302 which opens to allow the medicament to be released. A person of ordinary skill in the art in the field of the invention can appreciate that a variety of other release mechanisms can be employed to implement the described functions.

Figure 4A:
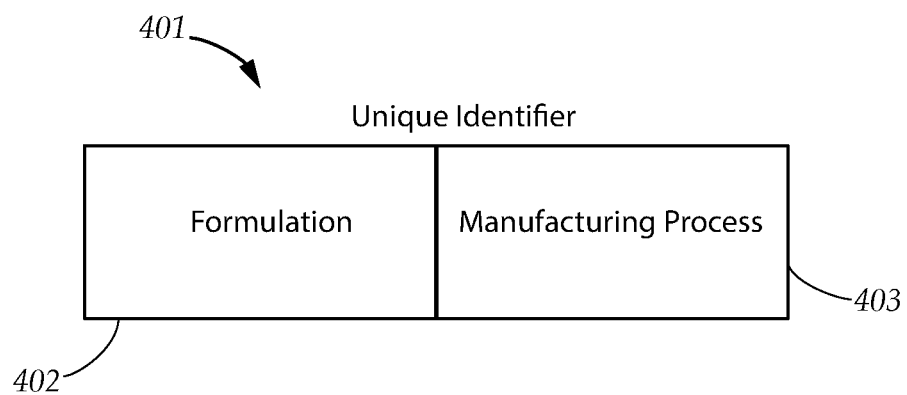
FIG. 4A is a block diagram depicting a unique identifier, in accordance with an embodiment of the present disclosure
Figure 4B:
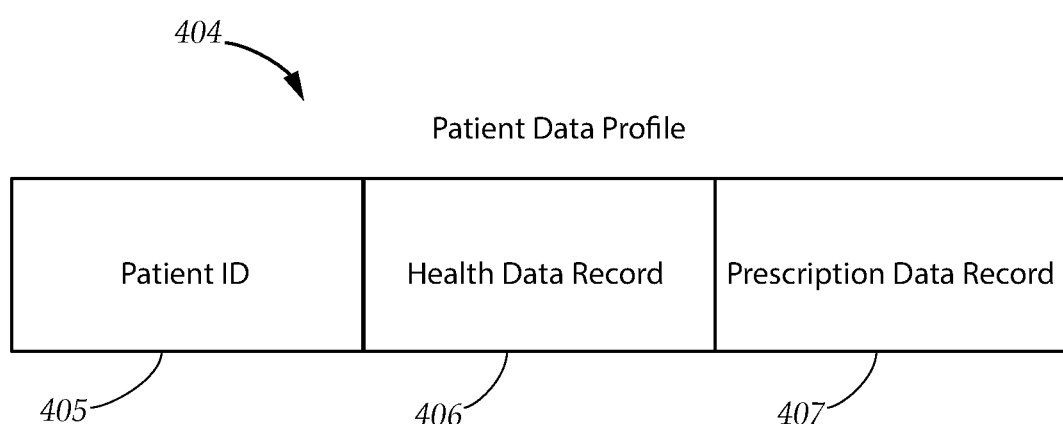
FIG. 4B is a block diagram depicting a patient data profile, in accordance with an embodiment of the present disclosure.

Data used by the system may be organized and stored in a database format. FIG. 4A depicts an example of a unique identifier 401 encoded within a programmable encapsulation wherein the unique identifier comprises a sequence of bytes of data formatted as a database record. The unique identifier further comprises a plurality of formulation data fields 402, and a plurality of manufacturing process data fields 403. The formulation data fields describe the compounds comprising the medicament, as well as the amount of each compound, along with any other information that may be relevant to describing the formulation of the medicament. The manufacturing process data fields describe the identity of the manufacturer, the time of manufacture, the manufacturing facility, the expiration date of the medicament, and other relevant information. Each unique identifier is unique to a specific programmable encapsulation and allows each encapsulation to be tracked at all stages of its life cycle from manufacture to consumption. The patient's health data and prescription data are also stored in a database format. FIG. 4B depicts an example patient data profile 404 comprising a patient ID 405, a health data record 406, and a prescription data record 407. The patient ID identifies the patient, and can take the form of a name or alphanumeric sequence. The health data record comprises a plurality of fields each containing a different category of information relevant to the use of medicaments, such as a list of the patient's known allergies, medical conditions, a list of other medicaments being consumed, and other relevant health information. The prescription data record is comprised of a plurality of fields each containing a different category of information governing the use of the medicament as set forth by the prescriber, such as a formulation of the prescribed medicament, a dosage amount, a dosage schedule, a dosage window during which the medicament can be consumed comprising a start date and end date, a list of other medicaments that may cause a dangerous interaction with the prescribed medicament, and other relevant information. The described information contained within a unique identifier and a patient data profile can be stored in a variety of database formats, as can be appreciated by a person of ordinary skill in the art in the field of the invention.

Figure 5A:
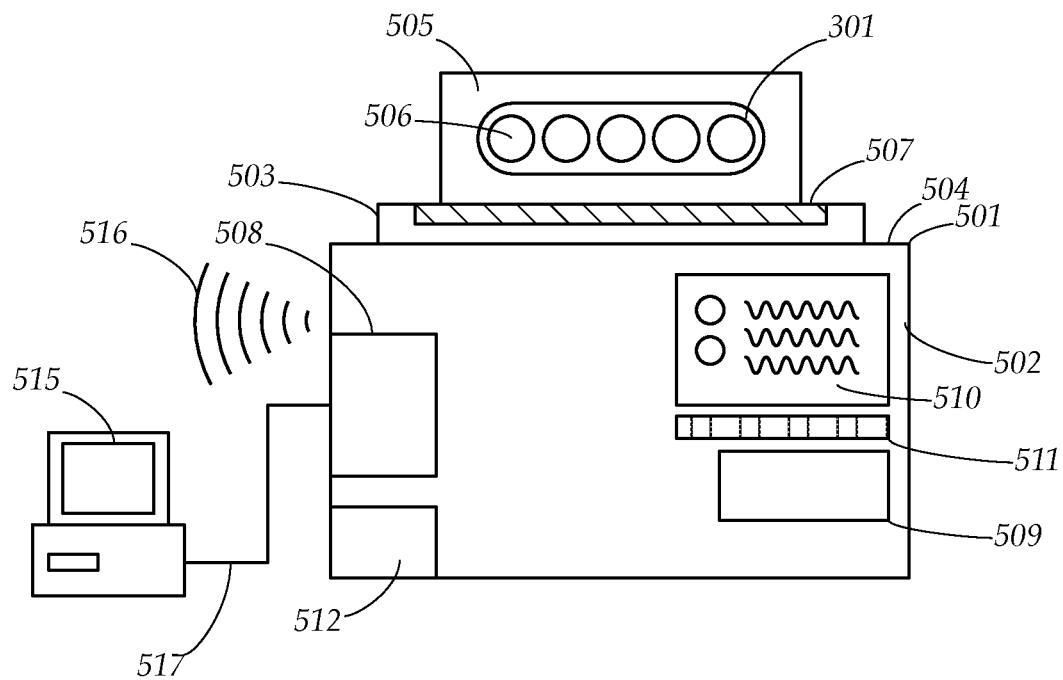
FIG. 5A is a diagrammatical side view of a programming device, in accordance with an embodiment of the present disclosure.

Turning now to FIG. 5A while also referring to FIG. 3, each programmable encapsulation is distributed to the dispensary without a patient data profile, and must be programmed using a programming device 501 before it can be used. The programming device 501 has a device housing 502 further provided with a programming area 503. The programming area 503 can be disposed on a top surface 504 of the device housing 502, allowing an encapsulation container 505 holding a group 506 of one or more of a programmable encapsulation 301 to be placed on the programming area 503. Encapsulations can be directly placed on the programming area 503 without a container 505. The programming area 503 may be disposed at different locations on or within the device housing 502, as can be appreciated by a person of ordinary skill in the art in the field of the invention. The programming area 503 is further configured with an RF reader/writer 507 adapted to read data transmitted by a programmable encapsulation 301 positioned on or in close proximity to the programming area, and write data to the encapsulation's programmable storage 311.

Figure 5B:
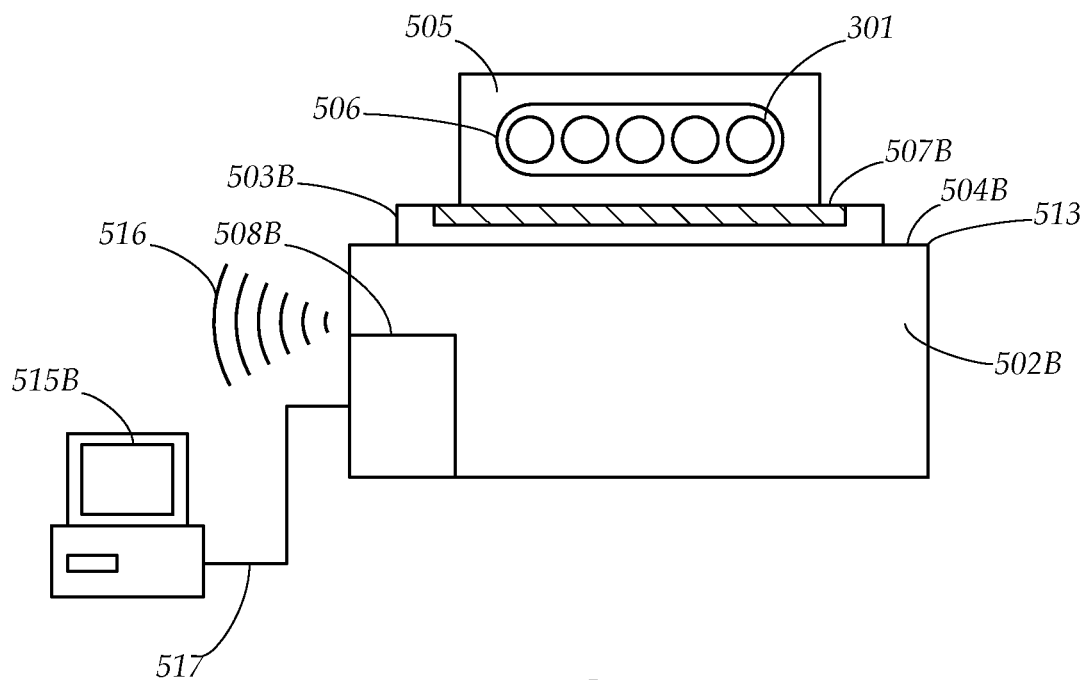
FIG. 5B is a diagrammatical side view of an alternate example of a programming device, in accordance with an embodiment of the present disclosure.

The RF reader/writer 507 can employ RFID technology, or another suitable transmission technology. The programmable storage on each encapsulation is protected to prevent unauthorized access either by encryption, password access, or a combination thereof. A legitimate dispensary will have programming devices equipped with the appropriate keys and/or passwords necessary for accessing the programmable storage. The programming device can be further configured with a communications module 508 to allow the programming device to communicate with a prescriber in order to receive a patient data profile, transmit information to the prescriber, or communicate with a computing device 515 which can be a personal computer, tablet computer, smartphone, or other portable computing device. The communications module can be configured to communicate wirelessly 516 via WIFI, Bluetooth, or other wireless technology, or via a wired connection 517 such as USB. In some embodiments, a programming device can connect directly to the internet. The programming device 501 further comprises a control module 509 for controlling the functions of the device, a display 510 which can also be a touchscreen for accepting input from a user, a plurality of input buttons 511 for accepting commands from the user, and a power source 512. Referring to FIGS. 5A-B simultaneously, FIG. 5B depicts an example of a streamlined programming device 513 comprising a streamlined device housing 502B with a top surface 504B, which is configured with a programming area 503B having an RF reader/writer 507B. The streamlined programming device is configured to perform the same role as the programming device 501, but the functions of the device are controlled by a computing device 515B connected to the streamlined programming device via a communications module 508B.

Figure 6:
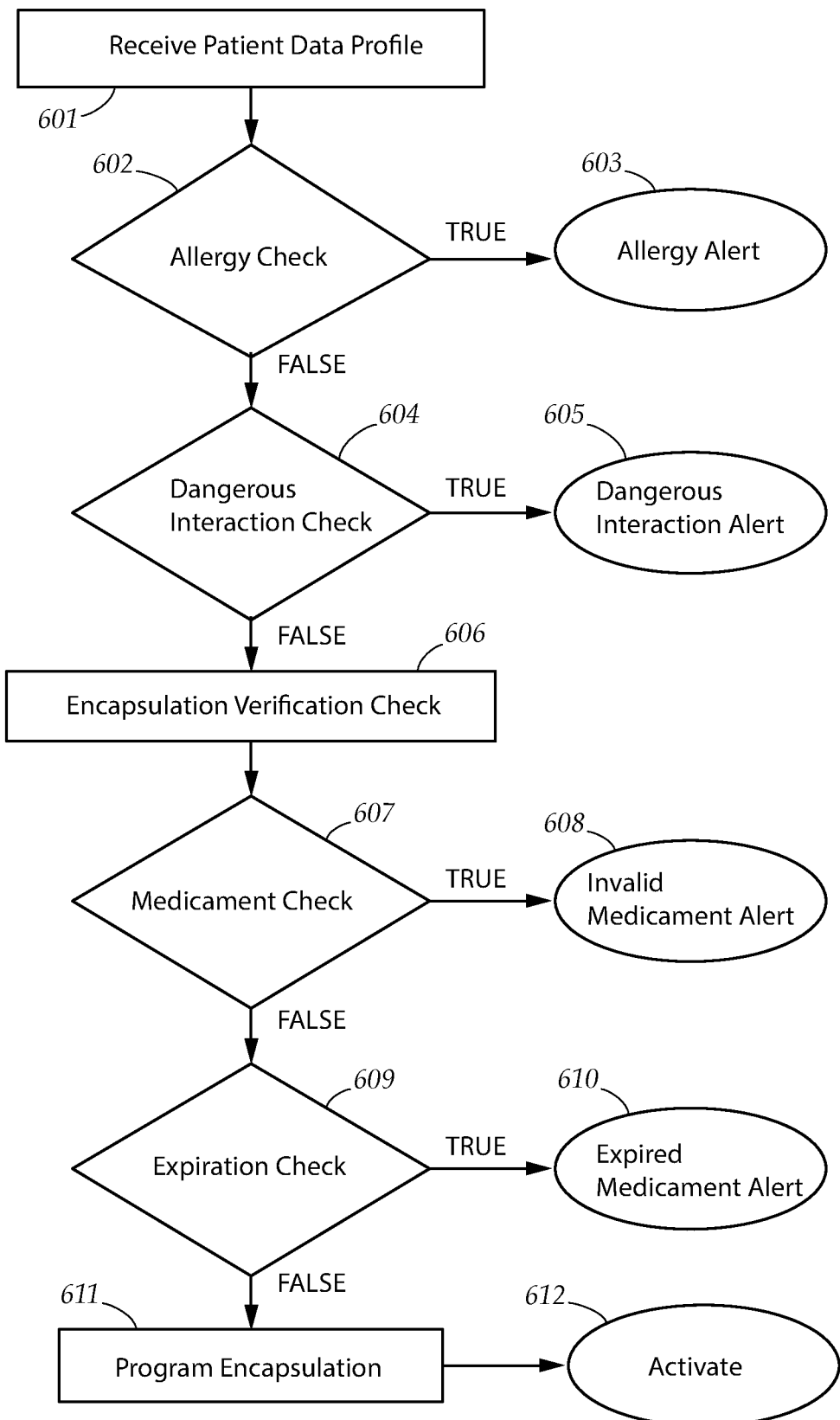
FIG. 6 is a flowchart depicting the process flow for the operation of the programming device, in accordance with an embodiment of the present disclosure.

FIG. 6 illustrates a programming process by which a programming device writes a patient data profile to a programmable encapsulation, in accordance with an aspect of an embodiment of the present disclosure. First, the programming device receives and reads a patient data profile 601 of a patient, where the patient data profile comprises a health data record and a prescription data record. The patient data profile can be received electronically from the prescriber, entered manually by a user into the programming device, or transmitted to the programming device using a computing device. In some cases, the prescriber may not have access to a list of other medicaments that the patient may be consuming. Therefore, the dispensary may retrieve a list of such medicaments from prescription records kept by the dispensary and edit the patient's health data accordingly. Next, the programming device performs an allergy check by comparing the formulation of the medicament found in the prescription data record with the allergy information in the health data record to determine if the patient is allergic to the prescribed medicament 602. If the patient is allergic to the medicament, the programming process ends and the programming device signals the user that the medicament cannot be dispensed due to a patient allergy. If no allergy is detected, the programming device performs a dangerous interaction check 604 by comparing the list of medicaments that may cause a dangerous interaction, with the list of other medicaments that are prescribed for the patient or which the patient is consuming, contained within the health data record. If the potential for a dangerous interaction exists between the prescribed medicament and another medicament consumed by the patient, the programming process ends and the programming device signals the user that the encapsulation cannot be dispensed due to a potential dangerous interaction 605. If no allergies or dangerous interactions are detected, the programming device performs an encapsulation verification check 606 comprising a medicament check 607 and expiration check 609. One or more of a programmable encapsulation containing the prescribed medicament are placed on or near the programming area of the programming device, and the RF reader/writer proceeds to read the data encoded within each encapsulation in the programming area. The programming device performs a medicament check 607 by reading the unique identifier for each encapsulation within the programming area. If the programming device detects an encapsulation with a formulation which differs from the prescription data, or if the programming device detects an encapsulation with an invalid unique identifier (such as a counterfeit encapsulation), the programming process ends and the programming device signals the user that the encapsulation cannot be dispensed due to an invalid medicament 608. If no invalid medicaments are detected, the programming device performs an expiration check 609 by comparing the current date with the expiration date contained in the manufacturing process data fields for each programmable encapsulation in the programming area. If any encapsulation is detected with an expiration date that has already passed or will pass within the dosage window specified in the prescription data, the programming process ends and the programming device signals the user that the encapsulation cannot be dispensed because it has or will expire 610. After the encapsulation verification check is complete, the programming device proceeds to program 611 each encapsulation in the programming area by writing the patient data profile onto the programmable storage of each programmable encapsulation. Referring to FIG. 3 while continuing to refer to FIG. 6, the programming device can also be configured to set the clock within an encapsulation's processing unit 306. Once an encapsulation has been programmed with a complete patient data profile, it is then activated 612 and ready to be used, and can be dispensed to the patient.

Figure 7:
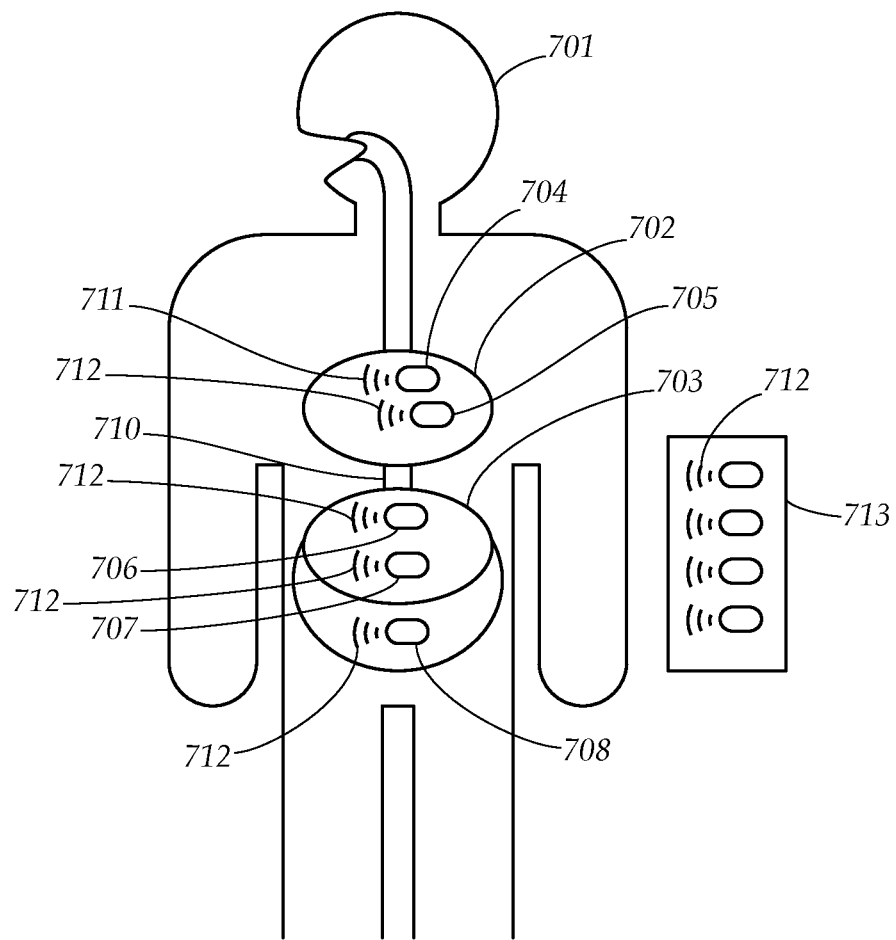
FIG. 7 is a diagrammatical representation of the interaction of a plurality of programmable encapsulations within a patient's body, in accordance with an embodiment of the present disclosure.

A programmable encapsulation is ready to be consumed once it is dispensed. FIG. 7 depicts a plurality of programmable encapsulations 704-708 which have been ingested by a patient 701 and which are currently located at various points in the patient's gastrointestinal tract 710. Each of the encapsulations 704-708 have been properly programmed and activated. The patient is also carrying a plurality of unconsumed encapsulations 713. The most recently ingested encapsulation 704 is depicted having entered the patient's stomach 702, and is in the process of transmitting an RF query signal 711. The previously ingested encapsulations 705-708 along with the unconsumed encapsulations 713 each detect the RF query signal and transmit an RF response signal 712 containing the unique identifier of each encapsulation, along with an ingestion state and release state. An encapsulation transmitting an RF response signal is referred to as a responding encapsulation. The ingestion state indicates whether the transmitting encapsulation has been ingested, which can be represented by a Boolean value, along with an ingestion time. The release state similarly indicates whether the transmitting encapsulation has released its enclosed medicament, and the release time. The encapsulation 704 sending the RF query receives the RF response signal from each responding encapsulation, and enters an operational process. The encapsulation 704 then determines, based on the ingestion state and release state of every responding encapsulation, how much medicament has been released and at what time each release occurred. This data is then referenced against the dosage schedule contained within the encapsulation's prescription data record. The encapsulation 704 will then calculate whether it can release its contained medicament without causing an incorrect dose or an overdose. The encapsulation 704 will also determine whether any of the other ingested encapsulations 705-708 contain a medicament that can cause a dangerous interaction with its enclosed medicament. If the enclosed medicament cannot be released without causing a potential incorrect dose or overdose, or if the release could cause a dangerous interaction with another medicament, then the encapsulation will enter into a deactivated state.

Figure 8:
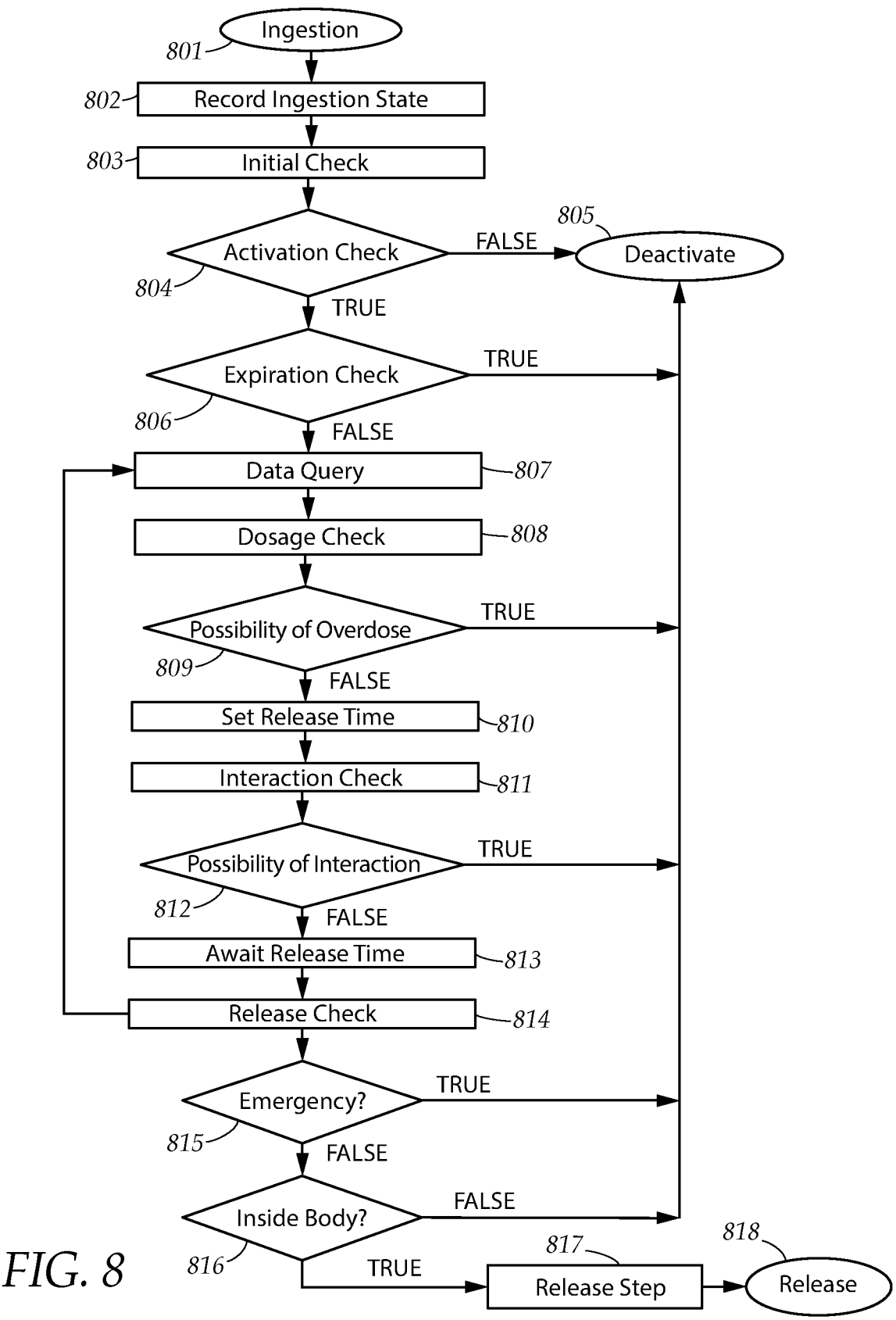
FIG. 8 is a flowchart depicting the process flow governing the release of a medicament by a programmable encapsulation, according to an embodiment of the present disclosure.

FIG. 8 depicts the operational process flow for a programmable encapsulation in accordance with an embodiment of the present disclosure. Referring to FIG. 3 alongside FIG. 8, the programmable encapsulation 301 is equipped with a sensor module 309 configured to detect whether the encapsulation has been ingested, such as by detecting the presence of stomach acid. Once the encapsulation is ingested by a patient and reaches the stomach, the sensor module 309 signals the processing unit 306 that the encapsulation has been ingested. The processing unit recognizes that an ingestion event 801 has occurred, and begins the operational process. Next, the processing unit 306 sets the ingestion state to "true" and records the ingestion time 802 as indicated by the clock configured within the processing unit, and proceeds with an initial check 803 comprising an activation check 804 and an expiration check 806. The processing unit first performs an activation check 804 testing whether the programmable storage 311 contains a valid patient data profile. If the encapsulation has not been programmed with a patient data profile, or if the patient data profile contains invalid data, the processing unit will cause the encapsulation to deactivate 805 and cease operation. The deactivate step 805 also causes the processing unit to set the encapsulation's release state to "deactivated". If the activation check is successful, the processing unit performs an expiration check 806 by comparing the current time and date indicated by the clock with the encapsulation's expiration date and the dosage window contained in the prescription data record. If either the expiration date or the dosage window have passed, the processing unit will cause the encapsulation to deactivate 805. Once the expiration check is successful, the processing unit will initiate a data query 807 by activating the RF transceiver 307 and transmitting an RF query signal. All other programmable encapsulations that receive the RF query signal will transmit an RF response signal comprising the unique identifier of the responding encapsulation along with its status signal indicating its ingestion state and release state. The processing unit receives the RF response signals from each responding encapsulation and proceeds with a dosage check 808. The processing unit records the ingestion state and release state of each responding encapsulation and creates a time sequenced dose timeline which marks the formulation data, ingestion state, ingestion time, release state, and release time of each responding encapsulation. Responding encapsulations that have not been ingested will have an ingestion state value of "false", and can be ignored. Similarly, responding encapsulations with a release state of "deactivated" can also be ignored. It is possible for an encapsulation to have a release state value of "false", and have a release time scheduled at a future time. The processing unit then compares 809 the dose timeline with the dosage schedule contained in the encapsulation's prescription data record to determine whether its enclosed medicament can be released immediately without causing an overdose, or if the release time can be delayed in order to avoid an overdose. In some situations, the dosage schedule may allow for the release time to be delayed until a future time when the encapsulation will still be at a point in the patient's gastrointestinal tract where the medicament can be released and still be effective, whereas in other situations, a lengthy delay may not be possible or may result in the released medicament being ineffective. If the processing unit determines a time when the enclosed medicament can be safely released, the processing unit will set its release state to reflect the planned release time 810, which can be imminent or delayed. If the processing unit determines that there is no time when the medicament can be released safely and effectively, it will instead cause the encapsulation to deactivate 805. Once the dosage check 808 is complete, the processing unit will proceed with an interaction check 811 by comparing the dose timeline against the list stored within the prescription data record of medicaments that may cause a dangerous interaction with the enclosed medicament 812. If releasing its enclosed medicament may result in a dangerous interaction with another medicament that has already been released or which is scheduled to be released, the processing unit will cause the encapsulation to deactivate 805. If the interaction check 811 is successful, the processing unit will enter an awaiting release mode 813 until its release time. Once the release time arrives, the processing unit can perform an optional release check 814 and return to the data query step 807 and perform the dosage check 808 and interaction check 811 again. The processing unit may further check if an emergency condition 815 exists which can cause the encapsulation to deactivate. The processing unit may further perform a check 816 using the sensor module 309 to determine if the encapsulation is still within the patient's body, and deactivate the encapsulation and prevent release of any medicament if the encapsulation is outside of the body. If no further conditions exist which may interrupt the operational process, the processing unit will begin the medicament release step 817, mark its release state to "true", and cause the medicament component 303 to release the medicament 818. A person of ordinary skill in the art in the field of the invention will appreciate that the steps of the operational process can be reordered or modified to implement various embodiments of a system in accordance with the present disclosure.

Turning to FIG. 9, an example dose timeline 901 is depicted, based on the example shown in FIG. 7. The five encapsulations 704-708 are each represented by a row on the timeline 901, with the most recently ingested encapsulation 704 being represented by Row E, with the first ingested encapsulation 708 being represented by Row A. Each row has columns corresponding to the ingestion state and release state of each encapsulation. The current time 902 is given as 06:10, and the dosage schedule 903 is 10 mg every 4 hours. The encapsulation in Row A 904 was ingested at 01:00, and its medicament was released at 01:15. The patient then ingested two more encapsulations 905, 906, represented by Rows B and C, at 05:00 and 05:01 respectively. The encapsulation represented by Row B 905 released its medicament at 05:15. The encapsulation represented by Row C 906 set a release time of 09:15 in order to avoid an overdose of medicament. However, the patient then ingested two more encapsulations 907, 908 represented by Rows D and E, at 06:01 and 06:02 respectively. The encapsulation in Row D 907, in order to avoid causing an overdose, must delay the release of its medicament for at least 7 hours, and has been deactivated because the delay, in this situation, is too long. Similarly, the encapsulation in Row E 908 has also been deactivated.

In an alternate embodiment, each programmable encapsulation may be programmed with a release time corresponding to a fixed time window. The patient may receive a plurality of programmable encapsulations from the dispensary, where each encapsulation must be consumed at a certain date, time, or combination thereof. For example, a patient may receive seven programmable encapsulations with a dosage schedule of one encapsulation per day, where each encapsulation is assigned a dosage window of one day within the seven day schedule.

Figure 10:
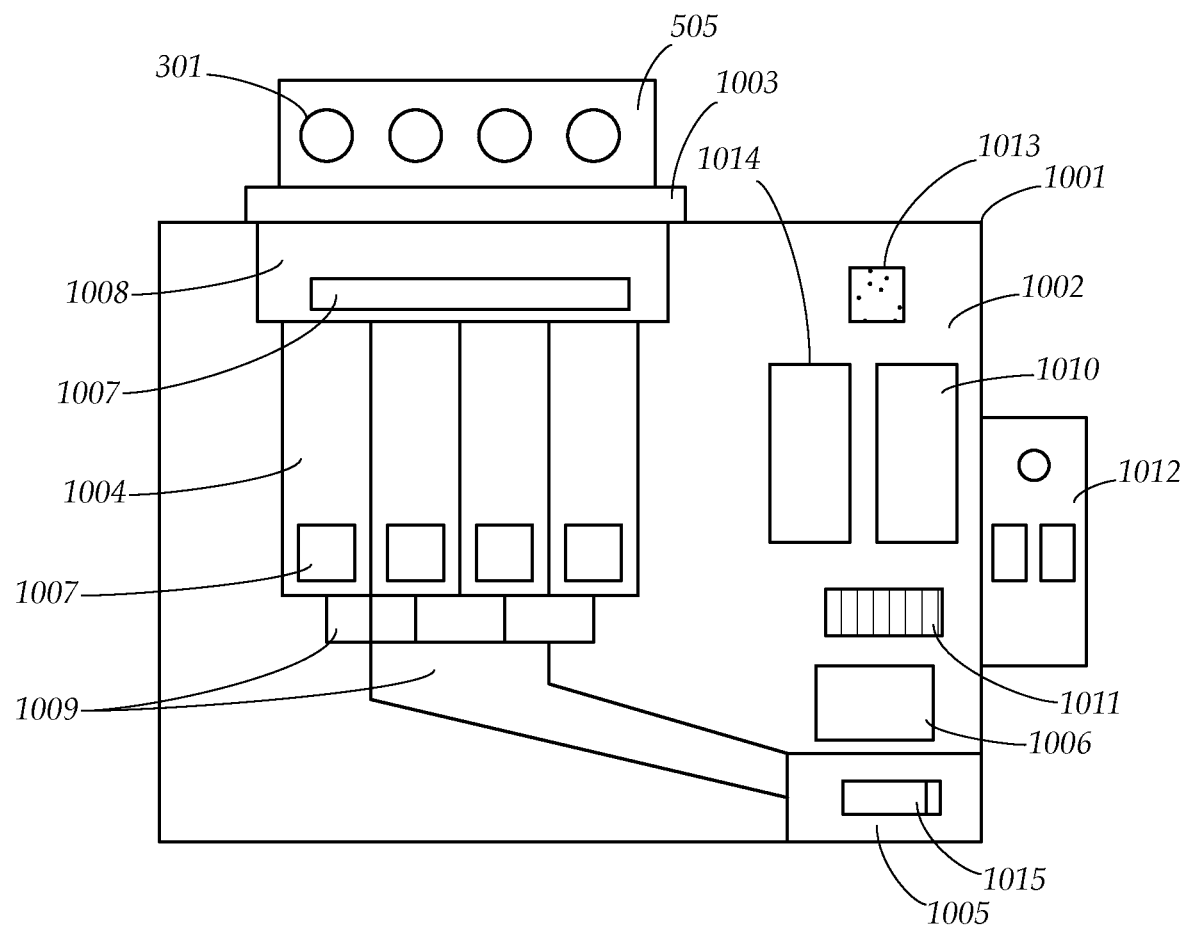
FIG. 10 is a diagrammatical cross section depicting a consumer encapsulation storage device, in accordance with an embodiment of the present disclosure.

After receiving the programmable encapsulations from the dispensary, the patient can store each encapsulation within a consumer encapsulation storage device. FIG. 10 depicts an example of a consumer encapsulation storage device 1001 in accordance with an aspect of an embodiment of the present disclosure. The consumer encapsulation storage device has a storage device housing 1002 configured with an intake mechanism 1003 for receiving one or more programmable encapsulations, one or more of a storage compartment 1004 capable of storing one or more programmable encapsulations, and a dispensing area 1005 for dispensing one or more stored programmable encapsulations. The consumer encapsulation storage device is further configured with a control module 1006 having a process and one or more of a memory for controlling the functions of the device, a display 1010 which can also be a touchscreen, and a plurality of input buttons 1011. The patient may feed one or more programmable encapsulations into the consumer encapsulation storage device by placing each encapsulation within the intake mechanism 1003. The intake mechanism can be configured to receive individual encapsulations, and can further be adapted to receive an encapsulation container 505 containing at least one of a programmable encapsulation 301. Each programmable encapsulation fed into the intake mechanism 1003 is then stored in one of the one or more of a storage compartment 1004. An inventory reader 1007 then reads the unique identifier and patient data profile stored within each programmable encapsulation. The control module then generates an inventory list identifying the number of stored encapsulations, and the unique identifier and the patient profile data of each encapsulation. The inventory reader can be configured as an RFID reader, or can be adapted to utilize another transmission technology. The consumer encapsulation storage device can further be configured with a plurality of inventory readers located at various positions within the storage device housing 1002. For example, an inventory reader 1007 can be positioned to read each encapsulation as it is fed into the intake mechanism 1003. In a consumer encapsulation storage device with more than one storage compartment 1004, an inventory reader 1007 can be positioned to read the contents of each storage compartment 1004. Where a consumer encapsulation storage device has more than one storage compartment, the consumer encapsulation storage device can be further configured with a sorting mechanism 1008 to organize and distribute one or more encapsulations between the plurality of storage compartments 1004. For example, programmable encapsulations containing medicaments with different formulations can be stored using different storage compartments to avoid intermixing the medicaments. The consumer encapsulation storage device is further configured with a feeding mechanism 1009 adapted to select and transport a programmable encapsulation from the one or more of a storage compartment 1004 to the dispensing area 1005. In a consumer encapsulation storage device with a plurality of storage compartments 1004, the feeding mechanism 1009 can be adapted to selectively transport one or more programmable encapsulations from one of the storage compartments 1004. The consumer encapsulation storage device can be further configured with a biometric authentication module 1012 equipped with one or more of a biometric sensor such as a fingerprint reader, facial recognition camera, iris scanner, retinal scanner, or other sensor for reading a biometric characteristic, a speaker 1013, and a communications module 1014. The consumer encapsulation storage device can also be equipped with a sterilization device for sterilizing encapsulations stored within a storage compartment.

The consumer encapsulation storage device can have one or more of a user profile, with each user profile being linked to a patient. The consumer encapsulation storage device can recognize whether an encapsulation has been prescribed to a patient by reading the patient ID within the patient data profile of each encapsulation. The inventory list further attributes each programmable encapsulation with the patient's user profile. The consumer encapsulation storage device can then generate a dispensing schedule with a series of dispensing times based on each patient's prescription data, and will alert a patient whenever it is time for the patient to consume a medicament, such as by emitting a sound through the speaker 1013. The consumer encapsulation storage device can employ the sorting and feeding mechanisms 1008, 1009 to select and group the appropriate encapsulations before the dispensing time arrives, to speed up the dispensing process. The patient can retrieve one or more programmable encapsulations from a consumer encapsulation storage device by undergoing a biometric authentication check using the biometric authentication module 1012. The consumer encapsulation storage device will not dispense any encapsulations unless the biometric authentication check succeeds, in order to prevent unauthorized access to the stored medicament. Once the patient has been authenticated, the consumer encapsulation storage device will dispense one or more of a programmable encapsulation via the dispensing area 1005 in accordance with the patient's prescription data. The patient may also request that the consumer encapsulation storage device dispense one or more encapsulations in advance, such as when the patient anticipates being unable to access the consumer storage during a future dispensing time, by entering an advance dispensing request containing a time duration. The consumer encapsulation storage device will then determine how many doses of medicament the patient will require for the requested time duration, and dispense the appropriate number of encapsulations.

In a preferred embodiment, the system incorporates measures that prevent the medicament enclosed within the programmable encapsulations from being consumed by a person who is not the patient for whom it was prescribed. A programmable encapsulation can be configured with an ingestion window which corresponds to a time interval, such as a period of three minutes, during which the patient must ingest the encapsulation. Once the ingestion window passes, the encapsulation will become deactivated. The consumer encapsulation storage device will set the ingestion window for each encapsulation as it is dispensed. A consumer encapsulation storage device can be configured with an RF reader/writer 1015 located at the dispensing area 1005 in order to write data to an encapsulation to set the ingestion window. A short ingestion window will make it more difficult for a patient to pass dispensed encapsulations to an unauthorized user. A programmable encapsulation can also be configured to check the identity of the patient as part of its operational process, to ensure that the medicament will not be released unless the encapsulation has been ingested by the patient for whom it was prescribed. Referring back to FIG. 8, the initial check 803 in the operational process can require the encapsulation to detect an identifying signal from a patient identification device configured to uniquely identify a patient. A patient identification device can be implemented as an RFID tag worn by the patient or embedded under the patient's skin. A portable reader may also be configured to transmit an identifying signal and serve as a patient identification device.

Figure 11:
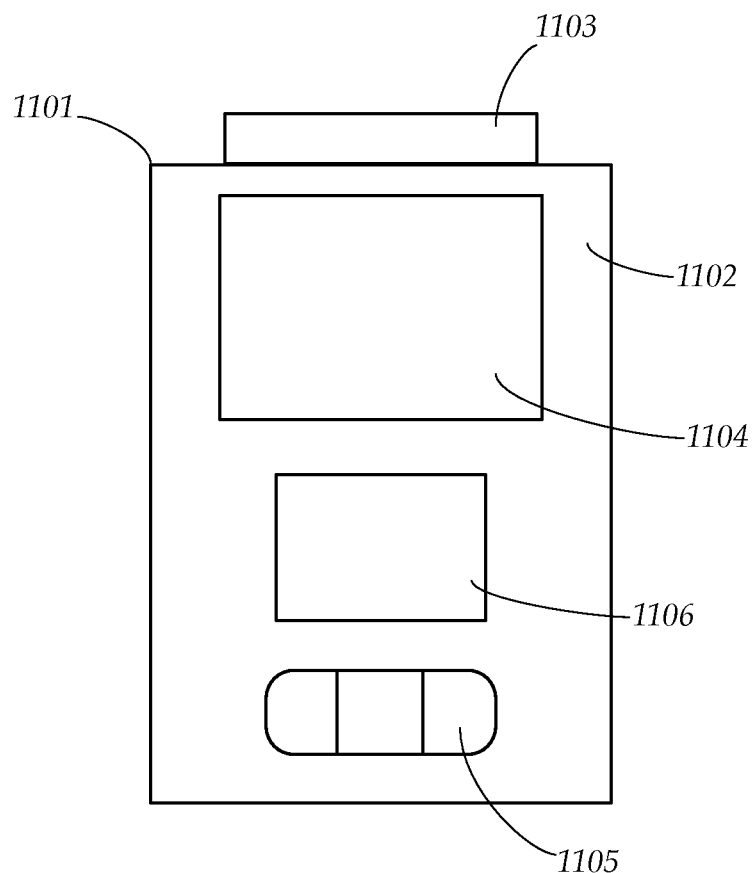
FIG. 11 is a diagrammatical front view of a portable reader device, in accordance with an embodiment of the present disclosure.

FIG. 11 depicts an example portable reader 1101 in accordance with an embodiment of the present disclosure. The portable reader 1101 has a reader housing 1102 which is compact and adapted to be held in a patient's hand. The portable reader further comprises an RF module 1103 such as an RFID reader, a display 1104 which can be a touchscreen for accepting input commands, and plurality of input buttons 1105. The portable reader can scan a programmable encapsulation and read its unique identifier and patient data profile. Information regarding the encapsulation's formulation and prescription data can then be viewed on the display 1104. As with the consumer encapsulation storage device, the portable reader can be configured to alert the patient when it is time for a medicament to be consumed. This allows the patient to manage and organize a supply of programmable encapsulations without using a consumer encapsulation storage device. Referring back to FIG. 7 while continuing to refer to FIG. 11, the portable reader can be further configured to transmit an RF query signal 711 and receive an RF response signal from any programmable encapsulations within RF transmission range, allowing the patient to identify and track the status of any ingested programmable encapsulations. The portable reader can also be programmed with the patient's identifying credentials, allowing it to transmit an identifying signal and serve as a patient identification device. Other embodiments of a portable reader can be configured with a biometric authentication module 1106 equipped with one or more biometric sensors such as a fingerprint reader, facial recognition camera, iris scanner, retinal scanner, or other sensor for reading a biometric characteristic, which would require a patient to undergo a biometric authentication check before the portable reader can transmit an identifying signal.

In an alternate embodiment, the system can be adapted for use with animals as well as human patients. Furthermore, the system can be adapted to administer consumables other than prescription medicaments, such as vitamins, nutrients, and non-prescription medicaments. A person of ordinary skill in the art of the field of the invention will appreciate that the described devices and methods can be adapted to implement the alternate embodiments described.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate or transport a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. Other types of languages include XML, XBRL and HTML5. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. Each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments of the present disclosure. In this regard, each block in the flowchart or block diagrams may represent a module, segment or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The flow diagrams depicted herein are just one example. There may be many variations to this diagram or the steps (or operations) described therein without departing from the spirit of the disclosure. For instance, the steps may be performed in a differing order and/or steps may be added, deleted and/or modified. All of these variations are considered a part of the claimed disclosure.

In conclusion, herein is presented a system for the tracking, dispensing, and administering of a medicament in a programmable encapsulation. The disclosure is illustrated by example in the drawing figures, and throughout the written description. It should be understood that numerous variations are possible, while adhering to the inventive concept. Such variations are contemplated as being a part of the present disclosure.

What is claimed is:

1. A medicament dispensing and administering system for a medicament intended for consumption by a patient having a digestive system, the patient further having a patient data profile comprising prescription data and a health data record listing the patient's allergies as well as a list of other medicaments prescribed for the patient, the prescription data defines a prescribed medicament along with a list of other medicaments which would cause a harmful interaction with the prescribed medicament, and contains a dosage schedule having one or more scheduled dose times, the system comprising:

at least one programmable encapsulation adapted to be ingested by the patient, the programmable encapsulation has a shell, a medicament chamber, a sensor module, and a control module, the shell encloses the medicament component and the control module, the sensor module is adapted to detect an ingestion event indicating the ingestion of the programmable encapsulation by the patient, the medicament component is adapted to store the medicament and selectively release the medicament through the shell, the control module controls the selective release of the medicament by the medicament component at one of the scheduled dose times after detecting the ingestion event, the control module has an RF transceiver, a permanent storage containing formulation data which describes the formulation of the medicament as well as a medicament expiration date, and a programmable storage;

a programming device having an RF reader and writer adapted to write the patient data profile to the programmable storage, read the formulation data of the medicament stored within the programmable encapsulation and activate the programmable encapsulation after verifying that the medicament matches the prescribed medicament, the programming device is further adapted to compare the formulation of the medicament stored within the programmable encapsulation with the health data record and the prescription data to identify a potential allergic reaction or harmful interaction, the programming device is further adapted to prevent the programmable encapsulation from being activated upon detecting that the medicament does not match the prescribed medicament, that the patient is allergic to the medicament, that the medicament is expired, or upon identifying the potential harmful interaction between the medicament and the list of other medicaments prescribed for the patient;

an encapsulation storage device having a storage device control module, a storage compartment for storing at least one of the programmable encapsulation, an inventory reader adapted to read the formulation data and the patient data profile contained in each programmable encapsulation, a biometric authentication module adapted to verify the identity of the patient by reading a biometric characteristic which uniquely identifies the patient for whom the medicament is prescribed, and a feeding mechanism adapted to dispense the programmable encapsulation within the storage compartment, wherein the storage device control module is adapted to dispense each programmable encapsulation according to a dispensing schedule after first verifying the identity of the patient, the dispensing schedule having a plurality of dispensing times whereby each dispensing time occurs before one of the scheduled dose times, the encapsulation storage device further has an RF writer adapted to write to the programmable storage of each programmable encapsulation upon dispensing said programmable encapsulation and define an ingestion window corresponding to a period of time;

a personal identification device adapted to transmit a patient identifying signal which is uniquely associated with the patient;

a portable reader having an RF module and a display, the RF module is adapted to read the formulation data and the prescription data of the programmable encapsulation, allowing the patient to view the formulation data and prescription data via the display, the portable reader is further adapted to transmit the patient identifying signal, as well as alert the patient prior to each scheduled dose time;

wherein the programmable encapsulation is adapted to enter a deactivated state upon detecting the occurrence of the ingestion event unless the programmable encapsulation is activated by the programming device, the programmable encapsulation is further adapted to determine the presence of a previously ingested programmable encapsulation within the digestive system of the patient by transmitting an RF query, and each previously ingested programmable encapsulation is adapted to transmit an RF response signal to the programmable encapsulation upon receiving the RF query, the RF response signal identifies the formulation of the medicament stored within the previously ingested programmable encapsulation, and the programmable encapsulation is adapted to avoid an overdose by entering into the deactivated state upon detecting the presence of the same medicament stored within the previously ingested programmable encapsulation, the programmable encapsulation is further adapted to enter the deactivated state upon identifying a potential harmful interaction between the medicament within the programmable encapsulation and the medicament stored within the previously ingested programmable encapsulation, the programmable encapsulation is further adapted to enter into the deactivated state upon the elapsing of the ingestion window;

wherein the programmable encapsulation is further adapted to receive the patient identifying signal, and the programmable encapsulation is further adapted to enter the deactivated state upon detecting the ingestion event unless the programmable encapsulation receives the patient identifying signal associated with the patient; and wherein the portable reader is further adapted to identify each previously ingested programmable encapsulation and the formulation of the medicament stored therein by transmitting the RF query and receiving the RF response signal from each previously ingested programmable encapsulation.

* * * * *